US010877025B2

(12) United States Patent
Kortazar Zabala et al.

(10) Patent No.: US 10,877,025 B2
(45) Date of Patent: Dec. 29, 2020

(54) FLUORESCENT FUSION POLYPEPTIDE, ENCODING NUCLEIC ACID, AND CELL COMPRISING SAID POLYPEPTIDE

(71) Applicant: INNOVATIVE TECHNOLOGIES IN BIOLOGICAL SYSTEMS S.L., Derio (ES)

(72) Inventors: Danel Kortazar Zabala, Algorta-Getxo (ES); Aida Clarisa Salado Pogonza, Bilbao (ES); Jorge Gámiz Mata, Ermua (ES); Meritxell Roura Ferrer, Vizcaya (ES); Rosa Mella López, Portugalete (ES); Patricia Villacé Lozano, Etxebarri (ES)

(73) Assignee: INNOVATIVE TECHNOLOGIES IN BIOLOGICAL SYSTEMS S.L., Derio (ES)

( * ) Notice: Subject to any disclaimer, the term of this patent is extended or adjusted under 35 U.S.C. 154(b) by 0 days.

(21) Appl. No.: 15/708,971

(22) Filed: Sep. 19, 2017

(65) Prior Publication Data

US 2018/0003697 A1 Jan. 4, 2018

Related U.S. Application Data

(62) Division of application No. 14/412,513, filed as application No. PCT/EP2013/064400 on Jul. 8, 2013, now Pat. No. 9,784,728.

(30) Foreign Application Priority Data

Jul. 6, 2012 (EP) .................................... 12382272

(51) Int. Cl.
*C07K 19/00* (2006.01)
*G01N 33/50* (2006.01)
*C07K 14/715* (2006.01)

(52) U.S. Cl.
CPC ..... *G01N 33/5035* (2013.01); *C07K 14/7155* (2013.01); *C07K 2319/03* (2013.01); *C07K 2319/04* (2013.01); *C07K 2319/60* (2013.01); *C07K 2319/70* (2013.01)

(58) Field of Classification Search
None
See application file for complete search history.

(56) References Cited

U.S. PATENT DOCUMENTS

| 6,197,928 | B1 | 3/2001 | Tsien et al. |
| 7,192,932 | B1 | 3/2007 | Tasken et al. |
| 9,784,728 | B2 | 10/2017 | Kortazar Zabala et al. |
| 2009/0176239 | A1* | 7/2009 | Kim ................... C07K 14/4728 435/6.14 |
| 2018/0003698 | A1 | 1/2018 | Kortazar Zabala et al. |

FOREIGN PATENT DOCUMENTS

EP 1571448 A1 9/2005

OTHER PUBLICATIONS

Komada et al. Early calcium signaling and calcium requirements for the IL-2 receptor expression and IL-2 production in stimulated lymphocytes. Cell Immunol. Nov. 1, 1996;173(2):215-20.*
Hara et al., Imaging endoplasmic reticulum calcium with a fluorescent biosensor in transgenic mice. Am J Physiol Cell Physiol. Oct. 2004;287(4):C932-8.
Mank et al., Genetically encoded calcium indicators. Chem Rev. May 2008;108(5):1550-64.
Miyawaki et al., Fluorescent indicators for Ca2+ based on green fluorescent proteins and calmodulin. Nature. Aug. 28, 1997:388(6645):882-7.
Nakai et al., A high signal-to-noise Ca(2+) probe composed of a single green fluorescent protein. Nat Biotechnol. Feb. 2001;19(2):137-41.
Rodriguez, cAMP Regulates IL-2 Receptor Signaling in Human T Cells. A Dissertation Presented to the Faculty of The University of Texas Health Science Center at Houston and The University of Texas M.D. Anderson Cancer Center Graduate School of Biomedical Sciences in Partial Fulfillment of the Requirements for the Degree of Doctor of Philosophy. 24 pages, Dec. 2008.
Rudolf et al., Looking forward to seeing calcium. Nat Rev Mol Cell Biol. Jul. 2003;4(7):579-86.
Ruehr et al., Cyclic AMP-dependent protein kinase binding to A-kinase anchoring proteins in living cells by fluorescence resonance energy transfer of green fluorescent protein fusion proteins. J Biol Chem. Nov. 12, 1999;274 (46):33092-6.
Shigetomi et al., Monitoring astrocyte calcium microdomains with improved membrane targeted GCaMP reporters. Neuron Glia Biol. Aug. 2010;6(3):183-91.
Snapp, Design and use of fluorescent fusion proteins in cell biology. Curr Protoc Cell Biol. Jul. 2005;Chapter 21:21.4.1-21.4.13.
Taylor et al., Multiplexed high content screening assays create a systems cell biology approach to drug discovery. Drug Discov Today Technol. 2005 Summer;2(2):149-54.
UniProtKB, P01589—IL2RA_Human. 10 pages, (1986).
International Search Report for Application No. PCT/EP2013/064400, dated Dec. 10, 2013. 8 pages.

* cited by examiner

*Primary Examiner* — Dong Jiang
(74) *Attorney, Agent, or Firm* — McCarter & English, LLP; Jill Ann Mello

(57) ABSTRACT

The present invention refers to a fluorescent fusion polypeptide capable of changing its localization within the cell from the cell cytoplasmic membrane to the retention vesicles, upon an increase in the concentration of second messengers within the cell cytoplasm, comprising a membrane localization peptide, a second messenger transduction protein binding peptide, a reticulum retention signal and a fluorescent peptide wherein: a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and b. the second messenger transduction protein binding peptide is physically bound, optionally through a linker, to the reticulum retention signal, which in turn is located at the C-terminus of the fluorescent fusion polypeptide.

8 Claims, 5 Drawing Sheets
Specification includes a Sequence Listing.

non-stimulated cells    stimulated cells

FLUORESCENT FUSION POLYPEPTIDE, ENCODING NUCLEIC ACID, AND CELL COMPRISING SAID POLYPEPTIDE

RELATED APPLICATIONS

This application is a divisional application of U.S. application Ser. No. 14/412,513, filed on Jan. 2, 2015, now U.S. Pat. No. 9,784,728, issued on Oct. 10, 2017; which is a 35 U.S.C. § 371 national stage filing of International Application No. PCT/EP2013/064400, filed on Jul. 8, 2013; which claims priority to European Patent Application No. 12382272.8, filed on Jul. 6, 2012. The entire contents of each of the foregoing applications are incorporated herein by reference.

FIELD OF THE INVENTION

The present invention pertains to the biotechnological field, particularly to a fluorescent fusion polypeptide, a biosensor comprising said polypeptide and uses thereof.

BACKGROUND OF THE INVENTION

The following discussion of the background of the invention is merely provided to aid the reader in understanding the invention, and is not admitted to describe or constitute prior art to the present invention.

High-content screening (HCS) in cell-based systems uses living cells as tools in biological research to elucidate the workings of normal and diseased cells. HCS is also used to discover and optimizes new drug candidates.

High content screening is a combination of modern cell biology, with all its molecular tools, with automated high resolution microscopy and robotic handling. Cells are first exposed to chemicals or RNAi reagents. Changes in cell morphology are then detected using image analysis. Changes in the amounts of proteins synthesized by cells are measured using a variety of techniques such as the green fluorescent proteins fused to endogenous proteins, or by fluorescent antibodies.

At a cellular level, parallel acquisition of data on different cell properties, for example activity of signal transduction cascades and cytoskeleton integrity is the main advantage of this method in comparison to the faster but less detailed high throughput screening. While HCS is slower, the wealth of acquired data allows a more profound understanding of drug effects. In this sense, one of the goals of HCS in the acquisition of data in connection to the activity of signal transduction cascades is to determine the effect of different drugs in the signalling processes through the measurement of intracellular second messenger levels.

Second messengers are molecules that relay signals from receptors on the cell surface to target molecules inside the cell, in the cytoplasm or nucleus. They relay the signals of hormones like epinephrine (adrenaline), growth factors, and others, and cause some kind of change in the activity of the cell. They greatly amplify the strength of the signal. Secondary messengers are a component of signal transduction cascades. Among these second messengers, the cAMP and calcium provide the paradigm for the second messenger concept and are appreciated as ubiquitous and critical intracellular molecules that regulate many key processes in the cell.

Ideally, said measurement requires tools of precise localization, high dynamic range and as little disturbance of cell physiology as possible that in turn are capable of monitoring the levels of second messengers in vivo by using a high content screening method.

For this, various fluorescent biosensors based on dynamically changing the fluorescent properties have been generated. In this sense, these types of biosensors are often based on a change in Fluorescent Resonance Energy Transfer (FRET). FRET is the process by which energy from an excited donor fluorophore is transferred to an acceptor fluorophore through radiationless dipole-dipole coupling. The efficiency of this energy transfer is highly dependent on the distance between (e.g. <10 nm for CFP/YFP) and the relative orientation of donor and acceptor fluorophore. However, FRET-based biosensors in the context of high content screening methods requires of a detection equipment of at least four filters, two for the excitation and two for the emission. In addition, due to the low intensity of the detection signal, the detection signal range and the screening sensibility are low. Lastly, the use of more than one fluorescence emission signal requires the use of more algorithms in order to correctly analyse the final signal.

Thus, there is still a need to develop improved methods or products for real time measurement of second messenger concentration within the dynamic environment of the living cell.

BRIEF DESCRIPTION OF THE INVENTION

A first aspect of the present invention refers to a fluorescent fusion polypeptide capable of changing its localization within the cell from the cell cytoplasmic membrane to the retention vesicles, upon an increase in the concentration of second messengers within the cell cytoplasm, comprising a membrane localization peptide, a second messenger transduction protein binding peptide, a reticulum retention signal and a fluorescent peptide wherein:
  a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and
  b. the second messenger transduction protein binding peptide is physically bound, optionally through a linker, to the reticulum retention signal, which in turn is located at the C-terminus of the fluorescent fusion polypeptide.

In another preferred embodiment of the first aspect of the invention, the membrane localization peptide is the extracellular domain of interleukin-2 receptor of SEQ ID No 17 or a variant which is at least 90% homologous to this sequence over the entire region based on amino acid identity and the reticulum retention signal is a peptide selected from the following list consisting of KDEL, HDEL, KKXX, KXKXX and RXR, wherein X is any aminoacid and wherein preferably said reticulum retention signal is KDEL.

In a more preferred embodiment of the first aspect of the invention, said second messenger transduction protein binding peptide is a cAMP transduction protein binding peptide, a calcium transduction protein binding peptide, an IP3 transduction protein binding peptide, a cGMP transduction protein binding peptide or a diacylglycerol transduction protein binding peptide. Thus in a further preferred embodiment of the invention, the fluorescent fusion polypeptide of the first aspect of the invention is capable of changing its localization within the cell from the cell cytoplasmic membrane to the retention vesicles, upon an increase in the concentration of a second messenger selected from the list consisting of calcium, cAMP, IP3, cGMP or diacyglycerol.

A second aspect of the invention refers to a fluorescent fusion polypeptide capable of changing its localization within the cell from the cell cytoplasmic membrane to the retention vesicles, upon an increase in the concentration of intracellular calcium, comprising a membrane localization peptide, a second messenger transduction protein binding peptide comprising a calmodulin binding sequence, a reticulum retention signal and a fluorescent peptide wherein:

a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide comprising the calmodulin binding sequence; and b. the second messenger transduction protein binding peptide is physically bound, optionally through a linker, to the reticulum retention signal, which in turn is located at the C-terminus of the fluorescent fusion polypeptide.

In a preferred embodiment of the second aspect of the invention, the calmodulin binding sequence is selected from the list consisting of SEQ ID No 1 (MEKRRWKKNFIA-VSAANRFKKISSSGAL), SEQ ID No 2 (AS-PWKSARLMVHTVATFNSI), SEQ ID No 3 (AIGFKK-LAEAVKFSAKLMGQ), SEQ ID No 4 (KKTFKEVANAVKISASLMGT), SEQ ID No 5 (GAVLKVLTTGLPALISWIKR), SEQ ID No 6 (RGGFR-RIARLVGVLREWAYR), SEQ ID No 7 (GGRLALL-RARLKELAALEAA) and SEQ ID No 8 (AE-GVRNIKSMWEKGNVFSSP) or a variant which is at least 90% homologous to any of these sequences over the entire region based on amino acid identity.

In a further preferred embodiment of the second aspect of the invention, the reticulum retention signal is a peptide selected from the following list consisting of KDEL, HDEL, KKXX, KXKXX and RXR, wherein X is any aminoacid and wherein preferably said reticulum retention signal is KDEL and/or the membrane localization peptide is the extracellular domain of interleukin-2 of SEQ ID No 17 or a variant which is at least 90% homologous to any of these sequences over the entire region based on amino acid identity.

In another preferred embodiment of the second aspect of the invention the fluorescent peptide is selected from the group consisting of GFP, YFP, turboGFP, tRFP and tRFP602.

In a still further preferred embodiment of the second aspect of the invention:

a. the calmodulin binding sequence is selected from the list consisting of SEQ ID No 1 (MEKRRWKKNFIA-VSAANRFKKISSSGAL), SEQ ID No 2 (AS-PWKSARLMVHTVATFNSI), SEQ ID No 3 (AIGFKKLAEAVKFSAKLMGQ), SEQ ID No 4 (KKTFKEVANAVKISASLMGT), SEQ ID No 5 (GAVLKVLTTGLPALISWIKR), SEQ ID No 6 (RGG-FRRIARLVGVLREWAYR), SEQ ID No 7 (GGR-LALLRARLKELAALEAA) and SEQ ID No 8 (AE-GVRNIKSMWEKGNVFSSP) or a variant which is at least 90% homologous to any of these sequences over the entire region based on amino acid identity;

b. the membrane localization peptide is the extracellular domain of interleukin-2 receptor of SEQ ID No 17 or a variant which is at least 90% homologous to this sequence over the entire region based on amino acid identity; and c. the reticulum retention signal is a peptide selected from the following list consisting of KDEL, HDEL, KKXX, KXKXX and RXR, wherein X is any aminoacid and wherein preferably said reticulum retention signal is KDEL.

In a still other preferred embodiment of the invention, the calcium fluorescent fusion polypeptide comprises or preferably consists of SEQ ID No 15.

A third aspect of the invention refers to a fluorescent fusion polypeptide capable of changing its localization within the cell from the cell cytoplasmic membrane to the retention vesicles, upon an increase in the concentration of intracellular cAMP, comprising a membrane localization peptide, a second messenger transduction protein binding peptide comprising a binding sequence to the RI and RII regulatory domains of PKA, a reticulum retention signal and a fluorescent peptide wherein:

a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and b. the second messenger transduction protein binding peptide is physically bound, optionally through a linker, to the reticulum retention signal, which in turn is located at the C-terminus of the fluorescent fusion polypeptide.

In a preferred embodiment of the third aspect of the invention, the binding sequence to the RI and RII regulatory domains of PKA is selected from the list consisting of SEQ ID No 9 (DLIEEAASRIVDAVIEQVKAAGAY), SEQ ID no 10 (VQGNTDEAQEELAWKIAKMIVSDVMQQ), SEQ ID No 11 (VQGNTDEAQEELLWKIAKMIVSDVMQQ), SEQ ID No 12 (FEELAWKIAKMIWSDVFQQ), SEQ ID No 13 (QIEYLAKQIVDNAIQQAK) and SEQ ID No 14 (LEQYANQLADQIIKEATE) or a variant which is at least 90% homologous to any of these sequences over the entire region based on amino acid identity.

In a further preferred embodiment of the third aspect of the invention, the reticulum retention signal is a peptide selected from the following list consisting of KDEL, HDEL, KKXX, KXKXX and RXR, wherein X is any aminoacid and wherein preferably said reticulum retention signal is KDEL and/or the membrane localization peptide is the extracellular domain of interleukin-2 of SEQ ID No 17 or a variant which is at least 90% homologous to any of these sequences over the entire region based on amino acid identity.

In another preferred embodiment of the third aspect of the invention, the fluorescent peptide is selected from the group consisting of GFP, YFP, turboGFP, tRFP and tRFP602.

In a still further preferred embodiment of the third aspect of the invention:

a. the binding sequence to the RI and RII regulatory domains of PKA is selected from the list consisting of SEQ ID No 9 (DLIEEAASRIVDAVIEQVKAAGAY), SEQ ID no 10 (VQGNTDEAQEELAWKIAK-MIVSDVMQQ), SEQ ID No 11 (VQGNTDEA-QEELLWKIAKMIVSDVMQQ), SEQ ID No 12 (FEELAWKIAKMIWSDVFQQ), SEQ ID No 13 (QIEYLAKQIVDNAIQQAK) and SEQ ID No 14 (LEQYANQLADQIIKEATE) or a variant which is at least 90% homologous to any of these sequences over the entire region based on amino acid identity;

b. the membrane localization peptide is the extracellular domain of interleukin-2 receptor of SEQ ID No 17 or a variant which is at least 90% homologous to this sequence over the entire region based on amino acid identity; and c. the reticulum retention signal is a peptide selected from the following list consisting of KDEL, HDEL, KKXX, KXKXX and RXR, wherein X is any aminoacid and wherein preferably the reticulum retention signal is KDEL.

In still another preferred embodiment of the third aspect of the invention, the fluorescent fusion polypeptide comprises or preferably consists of SEQ ID No 16.

A fourth aspect of the invention refers to a fluorescent fusion polypeptide capable of changing its localization within the cell from the cell cytoplasmic membrane to the retention vesicles, upon an increase in the concentration of Intracellular diacylglycerol, comprising a membrane localization peptide, a second messenger transduction protein binding peptide comprising a binding sequence to PKCδ, a reticulum retention signal and a fluorescent peptide wherein:

a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and b. the second messenger transduction protein binding peptide is physically bound, optionally through a linker, to the reticulum retention signal, which in turn is located at the C-terminus of the fluorescent fusion polypeptide.

In a preferred embodiment of the fourth aspect of the invention, the binding sequence to PKCδ is SEQ ID No 19 (AARKRKGSFFYGG), or a variant which is at least 90% homologous to this sequence over the entire region based on amino acid identity.

In a further preferred embodiment of the fourth aspect of the invention, the reticulum retention signal is a peptide selected from the following list consisting of KDEL, HDEL, KKXX, KXKXX and RXR, wherein X is any aminoacid and wherein preferably said reticulum retention signal is KDEL and/or the membrane localization peptide is the extracellular domain of interleukin-2 of SEQ ID No 17 or a variant which is at least 90% homologous to this sequence over the entire region based on amino acid identity.

In another preferred embodiment of the fourth aspect of the invention, the fluorescent peptide is selected from the group consisting of GFP, YFP, turboGFP, tRFP and tRFP602.

In a still further preferred embodiment of the fourth aspect of the invention:

a. the binding sequence to PKCδ is SEQ ID No 19 (AARKRKGSFFYGG), or a variant which is at least 90% homologous to this sequence over the entire region based on amino acid identity;

b. the membrane localization peptide is the extracellular domain of interleukin-2 receptor of SEQ ID No 17 or a variant which is at least 90% homologous to this sequence over the entire region based on amino acid identity; and c. the reticulum retention signal is a peptide selected from the following list consisting of KDEL, HDEL, KKXX, KXKXX and RXR, wherein X is any aminoacid and wherein preferably the reticulum retention signal is KDEL.

In still another preferred embodiment of the fourth aspect of the invention, the fluorescent fusion polypeptide comprises SEQ ID No 18.

A fifth aspect of the invention refers to a nucleic acid molecule comprising a polynucleotide sequence coding for a polypeptide as defined in any of the previous aspects of the invention.

A sixth aspect of the invention refers to a biosensor comprising the fusion polypeptide as defined in the first, second, third and fourth aspects of the invention.

A seventh aspect of the invention refers to a cell comprising the fluorescent fusion polypeptide as defined in any of the first, second, third or fourth aspects of the invention or the biosensor as defined in the sixth aspect of the invention, wherein preferably said cell is cell line U2O2.

In a further aspect, the present invention relates to several uses for the fluorescent fusion polypeptide as defined in any of the first, second, third or fourth aspects of the invention or of the biosensor as defined in the sixth aspect of the invention.

BRIEF DESCRIPTION OF THE DRAWINGS

The accompanying drawings, which are incorporated in and constitute a part of this specification, illustrate several embodiments and together with the description illustrate the disclosed compositions and methods.

DESCRIPTION OF THE INVENTION

Figure 1:
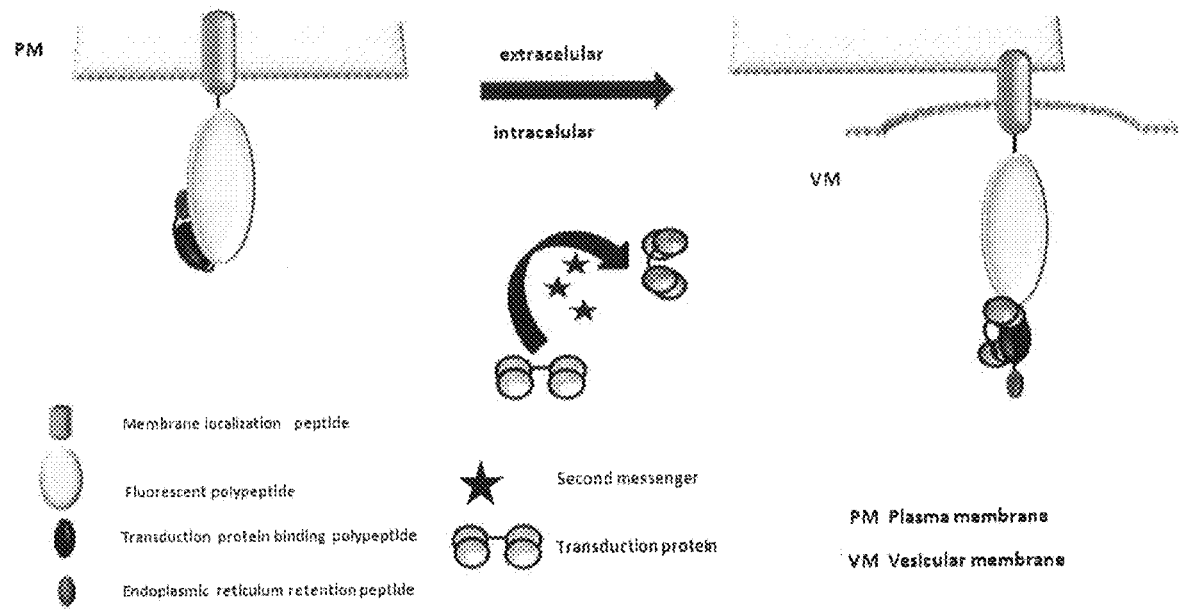
FIG. 1. Schematic representation of the fluorescent biosensor cellular localization model. Fluorescent biosensor changes its localization within the cell from the cell cytoplasmic membrane to the vesicles, upon an increase in the concentration of second messengers within the cell cytoplasm.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Definitions

In the context of the present invention, the term "fusion polypeptide" refers to a hybrid polypeptide comprising a combination of at least four peptides from different proteins that are combined into the same polypeptide structure.

In the context of the present invention, the term "membrane localization peptide" is intended to mean a peptide whose natural intracellular localization is in the plasma membrane.

As used herein, the term "transduction protein binding peptide" is intended to mean a peptide that is able to bind a transduction protein in a specific conformation. Therefore, this peptide is able to bind the transduction protein only when this transduction protein is interacting with a second messenger (cAMP, Ca2+, IP3, cGMP, diacylglycerol . . . ).

As used herein, the term "reticulum retention signal" is intended to mean a short peptide chain that directs the transport of the polypeptide to the endoplasmic reticulum and through the secretory pathway conferring thereby a multivesicular localization.

As used herein, the term "fluorescent peptide" is intended to mean a fluorescent peptide that has fluorescent capacities. Fluorescent peptide domains are characterized by having a specific excitation spectrum and emission spectrum.

In the context of the present invention, the linker has at least one amino acid residue, preferably at least two consecutive amino acid residues.

As used herein, the term "biosensor" is intended to mean a molecular tool or entity that is sensitive to, and can respond to, a physical or chemical stimulus and transmit information about cellular status.

As used herein, the term "drug" is intended to mean a molecule that potentially acts as an agonist or antagonist or modulator of a signalling pathway.

As used herein "stable cell line" is intended to mean a cell line that has been transfected or infected with a foreign piece of DNA that has incorporated itself into the genome of the cell.

As used herein "calmodulin binding sequence" is intended to mean the amino acid sequence corresponding to the calmodulin binding domain of the skeletal muscle myosin light chain kinase. This sequence is included in the basic 1-8-14 subclass of the 1-14 calmodulin binding motif. The consensus sequence of the basic 1-8-14 is (RK)(RK)(RK)(FILVW)xxxxxx(FAILVW)xxxxx(FILVW). These types of sequences can easily be found in the Calmodulin Binding Database (http://calcium.uhnres.utoronto.ca/ctdb/ctdb/home.htm).

As used herein "binding sequence to the RI and RII regulatory domains of PKA" is intended to mean the conserved amino acid sequence that is present in A-kinase anchor protein family (AKAP) and whose principal function is binding to the regulatory domain (RI or RII) of protein kinase A (PKA).

As used herein "HT31" is the peptide derived from human thyroid A-kinase anchoring protein (AKAP) that can destroy the anchorage of A-kinase (after activation by cAMP signal) by competing with AKAPs. HT31 binds to the two regulatory domains (RI and RII) of Protein Kinase A but its affinity for these domains is different: low for RI domain and high for RII domain.

As used herein "binding sequence to PKCdelta" is intended to mean the amino acid sequence corresponding to a synthetic soluble peptide which binds specifically to PKCdelta and no other PKCs. These types of sequences can be easily found in PKCLab Database (http://www.okclab.org/PKC/link/substrate_specificity.htm).

DETAILED DESCRIPTION OF THE INVENTION

The present invention confronts the problem of providing tools of precise localization, high dynamic range and as little disturbance of cell physiology as possible that are capable of monitoring a variation in the intracellular concentration levels of second messengers in vivo by using High-content screening (HCS) in cell-based systems, wherein these tools do not have the disadvantages of FRET-based biosensors.

In order to solve the above problem, the authors of the present invention designed a new fluorescent fusion polypeptide comprising a membrane localization peptide, a fluorescent peptide, a second messenger transduction protein binding peptide and a reticulum retention signal. This biosensor is formed by two peptides targeted to two different cellular compartments, allowing the measurement of the second messenger concentration by monitoring the distribution of the fluorescent polypeptide within the cellular cytoplasm. In this sense, the biosensor translocation within the cell shall be due to a change in its 3D conformation that hides or exposes the location signals in both ends of the polypeptide triggered by the binding of the transduction protein to the second messenger transduction protein binding peptide. In the basal state, the biosensor is located in one of the compartments; this means that the location peptide directed to the other cellular compartment is hidden by the 3D conformation. When the concentration of the second messenger is increased due to a cellular stimulation, these second messengers bind to the transduction protein that becomes active. The active transduction protein is able to bind to the transduction protein binding peptide in the biosensor causing a conformational change. At this point the spatial distribution of the different structural elements in the biosensor is modified and the location peptide directed to the other cellular compartment is exposed by the new-3D conformation so that the whole biosensor is transported to its new location at the new cellular compartment. All this process can be traced in living cells due to the presence of the fluorescent protein in the biosensor. A schematic view of the process can be visualized in the schematic representation shown in FIG. 1.

However, the authors of the present invention realized that the order of the peptides within the above mentioned fluorescent fusion polypeptide could not be placed arbitrarily within the polypeptide. This is the case since after numerous experiments the authors concluded that only one combination of elements provided the technical effect of transporting the biosensor to the other cellular compartment, such combination was:

a. the membrane localization peptide must be located at the N-terminus of the fluorescent fusion polypeptide and must be physically bound, optionally through a linker, to the fluorescent peptide, which in turn must be physically bound, optionally through a linker, to the second messenger transduction protein binding peptide; and b. the second messenger transduction protein binding peptide must be physically bound, optionally through a linker, to the reticulum retention signal, which in turn must be located at the C-terminus of the fluorescent fusion polypeptide.

The authors tested whether such biosensor having the above structure could be employ for detecting and quantifying different types of second messengers. As illustrated in examples 1-3 disclosed herein, the authors of the present invention constructed three different fluorescent fusion polypeptides, all of them comprising the extracellular domain of interleukin-2 receptor of SEQ ID No 17 as the membrane localization peptide, the peptide KDEL as the reticulum retention signal and the turboGFP as the fluorescent peptide. Thus, the only difference between these fluorescent fusion polypeptides lied on the type of second messenger transduction protein binding peptide used. In this sense, in the case of the calcium biosensor of example 1 the authors used a second messenger transduction protein binding peptide comprising a calmodulin binding domain, in the case of the cAMP biosensor of example 2 the authors used a second messenger transduction protein binding peptide comprising a protein kinase A (PKA) binding domain from A-kinase anchor protein (AKAP) and in the case of the diacylglycerol biosensor of example 3 the authors used a second messenger transduction protein binding peptide comprising the binding domain of SEQ ID No 19.

Surprisingly, the results shown in the examples and drawings presented herein by using the above fusion polypeptides of examples 1-3 indicated that an increased in the concentration of the second messenger induced a conformational change in the biosensor which promoted a redistribution of the fluorescent biosensor. The activity was calculated in all three cases as an increment of the granularity of the cells transfected with the biosensors of the invention. The fluorescence redistribution of the biosensor was detected by fluorescence using image analysis algorithms. Consequently, the variations in the second messenger concentrations can be monitored through this "hiding and exposition" process of location signals and the final localization of the biosensor.

Thus, a first aspect of the present invention refers to a fluorescent fusion polypeptide capable of changing its localization within the cell from the cell cytoplasmic membrane to the retention vesicles, upon an increase in the concentration of second messengers within the cell cytoplasm, comprising a membrane localization peptide, a second messenger transduction protein binding peptide, a reticulum retention signal and a fluorescent peptide wherein:

a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and b. the second messenger transduction protein binding peptide is physically bound, optionally through a linker, to the reticulum retention signal, which in turn is located at the C-terminus of the fluorescent fusion polypeptide.

In another preferred embodiment of the first aspect of the invention, the membrane localization peptide is the extracellular domain of interleukin-2 receptor of SEQ ID No 17 or a variant which is at least 90% homologous to this sequence over the entire region based on amino acid identity and the reticulum retention signal is a peptide selected from the following list consisting of KDEL, HDEL, KKXX, KXKXX and RXR, wherein X is any aminoacid and wherein preferably said reticulum retention signal is KDEL. In a more preferred embodiment of the first aspect of the invention, said second messenger transduction protein binding peptide is a cAMP transduction protein binding peptide, a calcium transduction protein binding peptide, an IP3 transduction protein binding peptide, a cGMP transduction protein binding peptide or a diacylglycerol transduction protein binding peptide. Thus in a further preferred embodiment of the invention, the fluorescent fusion polypeptide of the first aspect of the invention is capable of changing its localization within the cell from the cell cytoplasmic membrane to the retention vesicles, upon an increase in the concentration of a second messenger selected from the list consisting of calcium, cAMP, IP3, cGMP or diacyglycerol.

A second aspect of the invention refers to a fluorescent fusion polypeptide capable of changing its localization within the cell from the cell cytoplasmic membrane to the retention vesicles, upon an increase in the concentration of intracellular calcium, comprising a membrane localization peptide, a second messenger transduction protein binding peptide comprising a calmodulin binding sequence, a reticulum retention signal and a fluorescent peptide wherein:

a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide comprising the calmodulin binding sequence; and b. the second messenger transduction protein binding peptide is physically bound, optionally through a linker, to the reticulum retention signal, which in turn is located at the C-terminus of the fluorescent fusion polypeptide.

In a preferred embodiment of the second aspect of the invention, the calmodulin binding sequence is selected from the list consisting of SEQ ID No 1 (MEKRRWKKNFIA- VSAANRFKKISSSGAL), SEQ ID No 2 (ASPWKSARLMVHTVATFNSI), SEQ ID No 3 (AIGFKKLAEAVKFSAKLMGQ), SEQ ID No 4 (KKTFKEVANAVKISASLMGT), SEQ ID No 5 (GAVLKVLTTGLPALISWIKR), SEQ ID No 6 (RGGFRRIARLVGVLREWAYR), SEQ ID No 7 (GGRLALLRARLKELAALEAA) and SEQ ID No 8 (AEGVRNIKSMWEKGNVFSSP) or a variant which is at least 90% homologous to any of these sequences over the entire region based on amino acid identity.

In a further preferred embodiment of the second aspect of the invention, the reticulum retention signal is a peptide selected from the following list consisting of KDEL, HDEL, KKXX, KXKXX and RXR, wherein X is any aminoacid and wherein preferably said reticulum retention signal is KDEL and/or the membrane localization peptide is the extracellular domain of interleukin-2 of SEQ ID No 17 or a variant which is at least 90% homologous to any of these sequences over the entire region based on amino acid identity.

In another preferred embodiment of the second aspect of the invention the fluorescent peptide is selected from the group consisting of GFP, YFP, turboGFP, tRFP and tRFP602.

In a still further preferred embodiment of the second aspect of the invention:
a. the calmodulin binding sequence is selected from the list consisting of SEQ ID No 1 (MEKRRWKKNFIAVSAANRFKKISSSGAL), SEQ ID No 2 (ASPWKSARLMVHTVATFNSI), SEQ ID No 3 (AIGFKKLAEAVKFSAKLMGQ), SEQ ID No 4 (KKTFKEVANAVKISASLMGT), SEQ ID No 5 (GAVLKVLTTGLPALISWIKR), SEQ ID No 6 (RGGFRRIARLVGVLREWAYR), SEQ ID No 7 (GGRLALLRARLKELAALEAA) and SEQ ID No 8 (AEGVRNIKSMWEKGNVFSSP) or a variant which is at least 90% homologous to any of these sequences over the entire region based on amino acid identity;
b. the membrane localization peptide is the extracellular domain of interleukin-2 receptor of SEQ ID No 17 or a variant which is at least 90% homologous to this sequence over the entire region based on amino acid identity; and
c. the reticulum retention signal is a peptide selected from the following list consisting of KDEL, HDEL, KKXX, KXKXX and RXR, wherein X is any aminoacid and wherein preferably said reticulum retention signal is KDEL.

In a still other preferred embodiment of the invention, the fluorescent fusion polypeptide comprises or preferably consists of SEQ ID No 15.

A third aspect of the invention refers to a fluorescent fusion polypeptide capable of changing its localization within the cell from the cell cytoplasmic membrane to the retention vesicles, upon an increase in the concentration of intracellular cAMP, comprising a membrane localization peptide, a second messenger transduction protein binding peptide comprising a binding sequence to the RI and RII regulatory domains of PKA, a reticulum retention signal and a fluorescent peptide wherein:
a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and
b. the second messenger transduction protein binding peptide is physically bound, optionally through a linker, to the reticulum retention signal, which in turn is located at the C-terminus of the fluorescent fusion polypeptide.

In a preferred embodiment of the third aspect of the invention, the binding sequence to the RI and RII regulatory domains of PKA is selected from the list consisting of SEQ ID No 9 (DLIEEAASRIVDAVIEQVKAAGAY), SEQ ID no 10 (VQGNTDEAQEELAWKIAKMIVSDVMQQ), SEQ ID No 11 (VQGNTDEAQEELLWKIAKMIVSDVMQQ), SEQ ID No 12 (FEELAWKIAKMIWSDVFQQ), SEQ ID No 13 (QIEYLAKQIVDNAIQQAK) and SEQ ID No 14 (LEQYANQLADQIIKEATE) or a variant which is at least 90% homologous to any of these sequences over the entire region based on amino acid identity.

In a further preferred embodiment of the third aspect of the invention, the reticulum retention signal is a peptide selected from the following list consisting of KDEL, HDEL, KKXX, KXKXX and RXR, wherein X is any aminoacid and wherein preferably said reticulum retention signal is KDEL and/or the membrane localization peptide is the extracellular domain of interleukin-2 of SEQ ID No 17 or a variant which is at least 90% homologous to any of these sequences over the entire region based on amino acid identity.

In another preferred embodiment of the third aspect of the invention, the fluorescent peptide is selected from the group consisting of GFP, YFP, turboGFP, tRFP and tRFP602.

In a still further preferred embodiment of the third aspect of the invention:
a. the binding sequence to the RI and RII regulatory domains of PKA is selected from the list consisting of SEQ ID No 9 (DLIEEAASRIVDAVIEQVKAAGAY), SEQ ID no 10 (VQGNTDEAQEELAWKIAKMIVSDVMQQ), SEQ ID No 11 (VQGNTDEAQEELLWKIAKMIVSDVMQQ), SEQ ID No 12 (FEELAWKIAKMIWSDVFQQ), SEQ ID No 13 (QIEYLAKQIVDNAIQQAK) and SEQ ID No 14 (LEQYANQLADQIIKEATE) or a variant which is at least 90% homologous to any of these sequences over the entire region based on amino acid identity;
b. the membrane localization peptide is the extracellular domain of interleukin-2 receptor of SEQ ID No 17 or a variant which is at least 90% homologous to this sequence over the entire region based on amino acid identity; and
c. the reticulum retention signal is a peptide selected from the following list consisting of KDEL, HDEL, KKXX, KXKXX and RXR, wherein X is any aminoacid and wherein preferably the reticulum retention signal is KDEL.

In still another preferred embodiment of the third aspect of the invention, the fluorescent fusion polypeptide comprises or preferably consists of SEQ ID No 16.

A fourth aspect of the invention refers to a fluorescent fusion polypeptide capable of changing its localization within the cell from the cell cytoplasmic membrane to the retention vesicles, upon an increase in the concentration of intracellular diacylglycerol, comprising a membrane localization peptide, a second messenger transduction protein binding peptide comprising a binding sequence to PKCδ, a reticulum retention signal and a fluorescent peptide wherein:
a. the membrane localization peptide is located at the N-terminus of the fluorescent fusion polypeptide and is physically bound, optionally through a linker, to the fluorescent peptide, which in turn is physically bound, optionally through a linker, to the second messenger transduction protein binding peptide; and b. the second messenger transduction protein binding peptide is physically bound, optionally through a linker, to the reticulum retention signal, which in turn is located at the C-terminus of the fluorescent fusion polypeptide.

In a preferred embodiment of the fourth aspect of the invention, the binding sequence to PKCδ is SEQ ID No 19 (AARKRKGSFFYGG), or a variant which is at least 90% homologous to this sequence over the entire region based on amino acid identity.

In a further preferred embodiment of the fourth aspect of the invention, the reticulum retention signal is a peptide selected from the following list consisting of KDEL, HDEL, KKXX, KXKXX and RXR wherein x is any aminoacid and wherein preferably said reticulum retention signal is KDEL and/or the membrane localization peptide is the extracellular domain of interleukin-2 of SEQ ID No 17 or a variant which is at least 90% homologous to any of these sequences over the entire region based on amino acid identity.

In another preferred embodiment of the fourth aspect of the invention, the fluorescent peptide is selected from the group consisting of GFP, YFP, turboGFP, tRFP and tRFP602.

In a still further preferred embodiment of the fourth aspect of the invention:
a. the binding sequence to PKCδ is SEQ ID No 19 (AARKRKGSFFYGG), or a variant which is at least 90% homologous to this sequence over the entire region based on amino acid identity;
b. the membrane localization peptide is the extracellular domain of interleukin-2 receptor of SEQ ID No 17 or a variant which is at least 90% homologous to this sequence over the entire region based on amino acid identity; and
c. the reticulum retention signal is a peptide selected from the following list consisting of KDEL, HDEL, KKXX, KXKXX and RXR, wherein X is any aminoacid and wherein preferably the reticulum retention signal is KDEL.

In still another preferred embodiment of the fourth aspect of the invention, the fluorescent fusion polypeptide comprises SEQ ID No 18.

A fifth aspect of the invention refers to a nucleic acid molecule comprising a polynucleotide sequence coding for a polypeptide as defined in any of the previous aspects of the invention.

A sixth aspect of the invention refers to a biosensor comprising the fusion polypeptide as defined in the first, second, third and fourth aspects of the invention.

A seventh aspect of the invention refers to a cell comprising the fluorescent fusion polypeptide as defined in any of the first, second, third or fourth aspects of the invention or the biosensor as defined in the sixth aspect of the invention, wherein preferably said cell is cell line U2O2.

In a further aspect, the present invention relates to several uses for the fluorescent fusion polypeptide as defined in any of the first, second, third or fourth aspects of the invention or of the biosensor as defined in the sixth aspect of the invention. A first use of the biosensor according to the present invention is for detecting and quantifying second messengers including, but not limited thereto, cAMP, calcium, diacylglycerol, IP3 and cGMP. As already stated, binding of the second messenger to the fluorescent fusion polypeptide of any of the aspects of this invention results in a substantial change in the spatial conformation that leads to a change in the intracellular fluorescence localization. This fluorescence translocation can be harnessed for second messenger quantification by fluorescence microscopy. In addition, all this process can be traced in living cells due to the presence of the fluorescent protein in the biosensor.

The employment of the fluorescent fusion polypeptide as defined in any of the first, second, third or fourth aspects of the invention or the biosensor as defined in the sixth aspect of the invention further involves its use as a tool for drug screening.

In addition, the fluorescent fusion polypeptide as defined in any of the first, second, third or fourth aspects of the invention or the biosensor as defined in the sixth aspect of the invention is useful in the practice of essentially any application for which readout of second messenger transduction is obtained.

Such applications are well known in the art. However, mere exemplary applications of the present invention include but are not limited to:
a. Identifying test compounds that act as agonists, antagonists, inverse agonists or natural ligands of cell surface receptor selected from growth factors, cytokines, G-protein coupled receptors, integrins and calcium ion channels by studying the second messenger movement using fluorescence microscopy devices. In a preferred embodiment, said cell surface receptor is a G-protein coupled receptor (GPCR).
b. Expression cloning of peptide agonist, antagonist and inverse agonist of receptors.
c. Expression cloning of modulators that change the second messenger intracellular presence.
d. Establishing dose-response curves of membrane molecules modulators.
e. Determining alterations in membrane molecules and modulators involved in a disease or disorder which signalling cascade depends on these second messengers and thereby the biosensor can be used as a diagnostic tool.

In a preferred embodiment of the invention, the fluorescent fusion polypeptide as defined in any of the first, second, third or fourth aspects of the invention or the biosensor as defined in the sixth aspect of the invention can be used to generate stable cell lines which allow studying G-protein coupled receptors (GPCR), ion channels, and the activity of others proteins in living cells. The rapid translocation of the biosensor of the invention allows the quantification of GPCR and ion channel stimulation.

The fluorescent fusion polypeptide and the corresponding biosensor of the present invention can be made by techniques well known by those skilled in the art but as a way of example, they can be constructed as follows. The coding sequences corresponding to the membrane localization peptide, the fluorescent peptide, the protein transduction interacting peptide and the reticulum localization signal can be easily amplified by PCR and cloned into a shuttle plasmid. These coding sequences can be then easily cloned into the final fusion plasmid in the specific order presented herein using the restriction enzyme sites that flanked each sequence.

The following examples merely serve to illustrate the present invention.

EXAMPLES

Example 1. Construction and Use of a Calcium Biosensor for Measurement of Calcium in Living Cells within a Broad Dynamic Range of Physiological Concentrations of this Second Messenger The authors of the present invention constructed a fluorescent fusion polypeptide comprising the extracellular domain of interleukin-2 receptor of SEQ ID No 17 as the membrane localization peptide, the calmodulin binding domain from muscle myosin light chain kinase of SEQ ID No 1 as the second messenger transduction protein binding peptide, the peptide KDEL as the reticulum retention signal and the turboGFP as the fluorescent peptide wherein:
  a. the membrane localization peptide was located at the N-terminus of the fluorescent fusion polypeptide and was physically bound, through a linker, to the fluorescent peptide, which in turn was physically bound, through a linker, to the second messenger transduction protein binding peptide; and
  b. the second messenger transduction protein binding peptide was physically bound, through a linker, to the reticulum retention signal, which in turn is located at the C-terminus of the fluorescent fusion polypeptide.

The complete fluorescent fusion polypeptide is illustrated in SEQ ID No 15.

Figure 2:
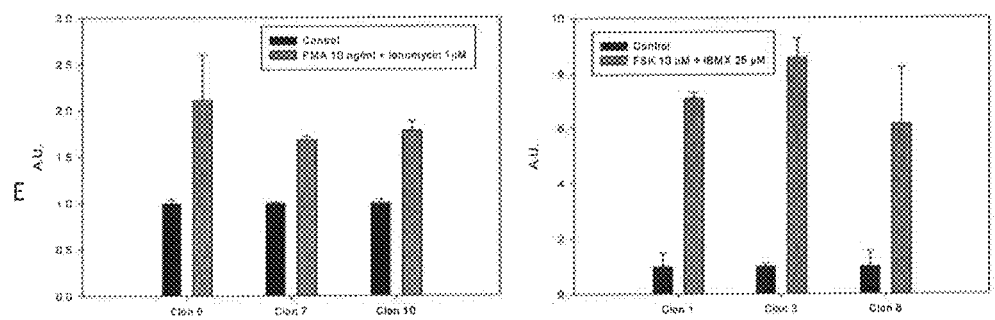
FIG. 2. Second messenger determination using the fluorescent biosensor. Increase in the second messenger concentration promotes a redistribution of the fluorescent biosensor. The change in the cellular fluorescence was calculated as an increment of the granularity of these cells. These same results were obtained with three different clones of the above cell lines as illustrated in this figure which provides proof of the reproducibility of these results corresponding to three clones containing the calcium biosensor (left graphic) or three clones containing the cAMP biosensor (right graphic).

In order to assess whether this polypeptide induces intracellular fluorescence redistribution in living cells, the turboGFP polypeptide was cloned as the fluorescent peptide and the cellular localization of the biosensor was analysed upon calcium induced activation. In this sense, cell lines HEK293 and U2O2 were stably transfected with the plasmid construction that contains the above mentioned biosensor's cDNA (please refer to SEQ ID No 15). After transfection, both cell lines presented a membrane distribution of the fluorescence. However, a substantial decrease in membrane distribution of the biosensor was observed after increasing the intracellular levels of calcium with 10 ng/ml of PMA and 1 uM of ionomycin. This result indicates that an increased in the concentration of intracellular calcium induces a conformational change in the biosensor which promotes a redistribution of the fluorescent biosensor. The activity was calculated as an increment of the granularity of these cells. These same results were obtained with three different clones of the above cell lines as illustrated in FIG. 2 (left graphic) which provides proof of the reproducibility of these results.

Secondly, in order to determine whether calcium induces a significant conformational change within a physiological dynamic range, the U2O2 biosensor stable cell line was stably transfected with the human Tachykinin receptor 1. The Tachykinin receptor 1 (TACR1) also known as Neurokinin 1 receptor (NK1R) or substance P receptor (SPR) Is a G protein coupled receptor found in the central nervous system and peripheral nervous system. The endogenous ligand for this receptor is Substance P, although it has some affinity for other Tachykinins, Substance P is synthesized by neurons and transported to synaptic vesicles; the release of Substance P is accomplished through the depolarizing action of calcium-dependent mechanisms. When NK1 receptors are stimulated, they can generate various second messengers, which can trigger a wide range of effector mechanisms that regulate cellular excitability and function. One of these mechanisms leads to the mobilization of calcium from both intra- and extracellular sources.

Figure 3:
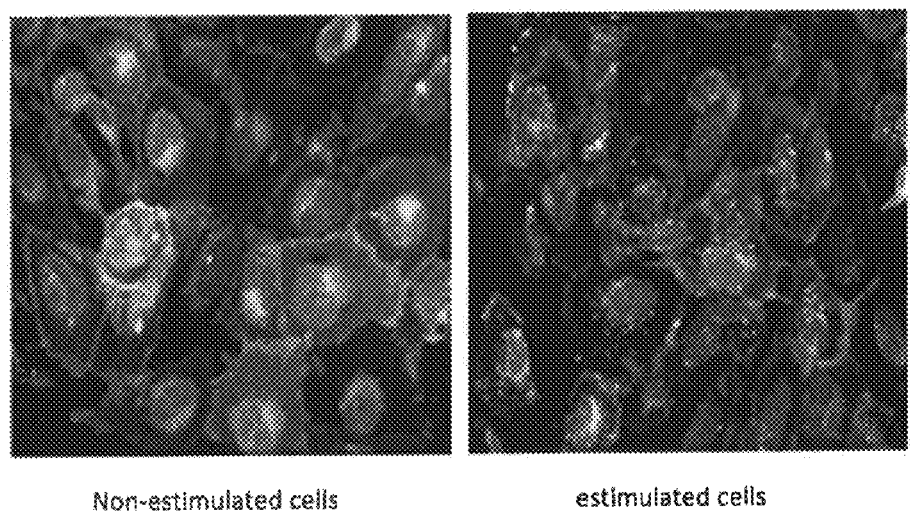
FIG. 3. Cellular distribution of calcium biosensor stimulated cells. U2OS, stably expressing human Neurokinin receptor 1 and fluorescent calcium biosensor, were stimulated with 10 uM of Substancia P agonist during 6 hours. After the treatment, the fluorescent biosensor was internalized in vesicles in the citosol. Human Neurikinin receptor 1 activity was determined measuring the generation of the vesicle using image analysis algorithms.
Figure 4:
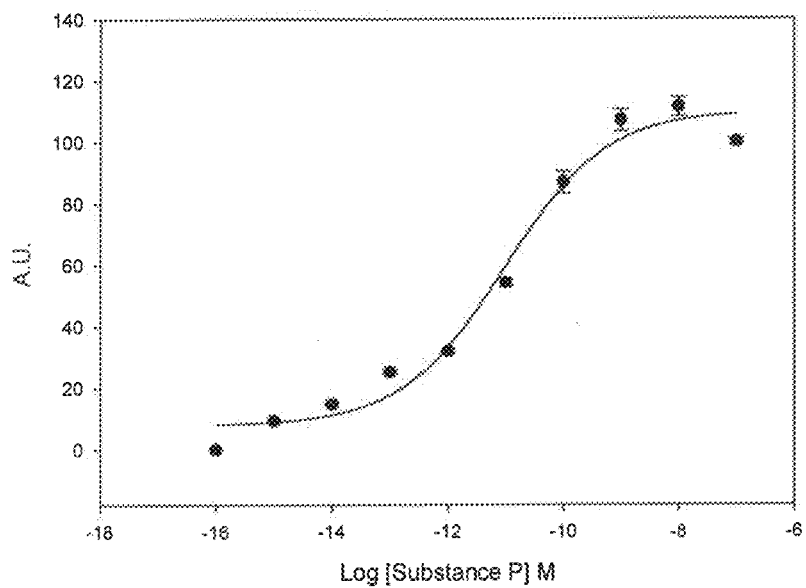
FIG. 4. Concentration response curve for Substancia P in Neurokinin 1 receptor-calcium biosensor cell line. Cells were treated with 10 log dilution series (n=4). The Ec50 for the Subtancia P was ~9.5×10$^{-12}$ M after a treatment of 6 h with agonist. Cells were fixed and the nuclei were stained with DAPI. % Activity was calculated relative to positive (10 uM). The internalization assay was validated with an average of Z'=0.85+/−0.01 for High Content Screening.

The double stable cell line was seeded at 20,000 cells per well on 96-mm optical plates, and cultured in 200 ul of DMEM F12 supplemented with 10% fetal bovine serum. For fluorescent biosensor redistribution, cells were stimulated with different concentrations of the agonist Substancia P during 6 hours. After treatment, the nucleus was stained with DAPI and biosensor fluorescence redistribution was detected by fluorescence using image analysis algorithms. When cells were treated with the agonist, the biosensor was internalized from plasmatic membrane in high intensity vesicles (FIG. 3). The activity was calculated as an increment of the granularity of these cells. Cells were treated with 11 log dilution series (n=5). The Ec50 for the Substance P was ~$9.5\times10^{-12}$ M after a treatment of 6 h with agonist. The redistribution assay was validated with an average of Z'=0.85+/−0.01 for High Content Screening (FIG. 4).

To check the biosensor sensibility in comparison with other methods, a typical fluorescent calcium assay was performed using Fura-2/AM ratiometric. Calcium increase inside the cell was measured using the ratio of the fluorescence from Fura2 bound and not bound to the ion. Cells were incubated with Fura2-AM and treated with increasing Substance P concentrations. Cells were treated with Substance P concentrations ranging from 0 to 10 μM by quadruplicate. The Ec50 for Substance P was ~1.4×10-8M. The calcium assay was validated with a Z'=0.84 for High Content Screening In both quantification methods, the image acquisition was performed using a "BD Pathway 855" High-Content Bio-Imager from BD Biosciences.

Example 2. Construction and Use of a cAMP Biosensor for Measurement of cAMP in Living Cells within a Broad Dynamic Range of Physiological Concentrations of this Second Messenger The authors of the present invention constructed a fluorescent fusion polypeptide comprising the extracellular domain of interleukin-2 receptor of SEQ ID No 17 as the membrane localization peptide, the protein kinase A (PKA) binding domain from A-kinase anchor protein (AKAP) of SEQ ID No 9 as the second messenger transduction protein binding peptide, the peptide KDEL as the reticulum retention signal and the turboGFP as the fluorescent peptide wherein:
  a. the membrane localization peptide was located at the N-terminus of the fluorescent fusion polypeptide and was physically bound, through a linker, to the fluorescent peptide, which in turn was physically bound, through a linker, to the second messenger transduction protein binding peptide; and
  b. the second messenger transduction protein binding peptide was physically bound, through a linker, to the reticulum retention signal, which in turn is located at the C-terminus of the fluorescent fusion polypeptide.

The complete fluorescent fusion polypeptide is illustrated in SEQ ID No 16.

As with the biosensor of Example 1, in order to assess whether the activation of the above mentioned polypeptide induces intracellular fluorescence redistribution in living cells, peptide turboGFP was cloned as the fluorescent peptide and the cellular localization of the biosensor was analysed upon cAMP induced activation. In this sense, cell lines SHSY5Y and U2O2 were stably transfected with the plasmid construction that contains the above mentioned biosensor's coding sequence. Both cell lines presented a membrane distribution of the fluorescence. As with Example 1, activity was calculated as an increment of granularity by treating these cells with 10 uM of forskolin and 25 uM of IBMX in three different stable clones during 36 h (FIG. 2 Right graphic).

Figure 5:
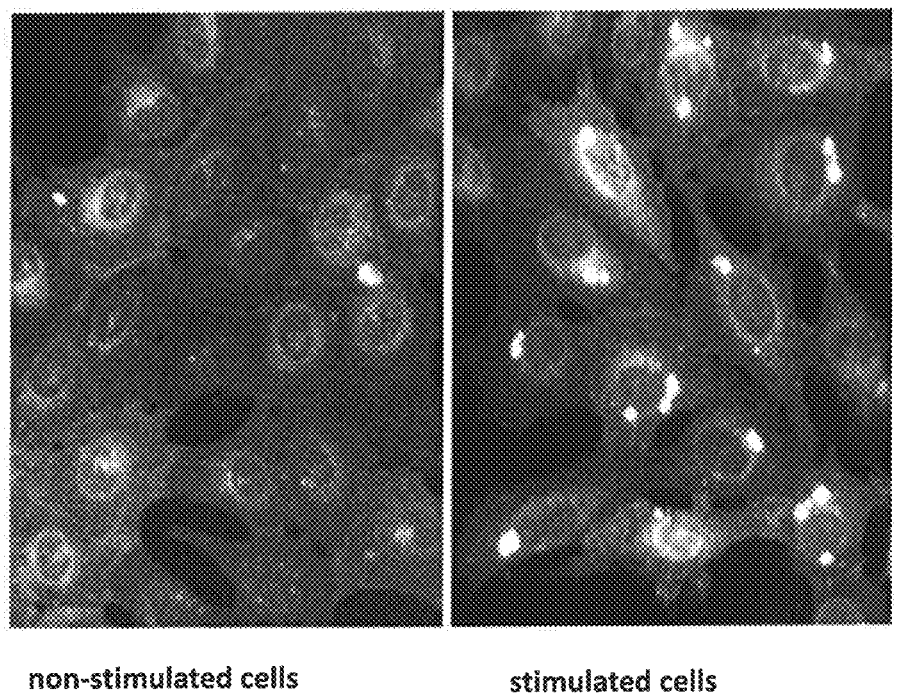
FIG. 5. Cellular distribution of cAMP biosensor stimulated cells. U2OS stably expressing human Adrenergic beta 2 receptor and fluorescent cAMP biosensor, were stimulated with 10 uM of Isoproterenol agonist during 36 hours. After the treatment, the fluorescent biosensor was internalized in vesicles in the citosol. Human Adrenergic beta 2 receptor activity was determined measuring the generation of the vesicle using image analysis algorithms.
Figure 6:
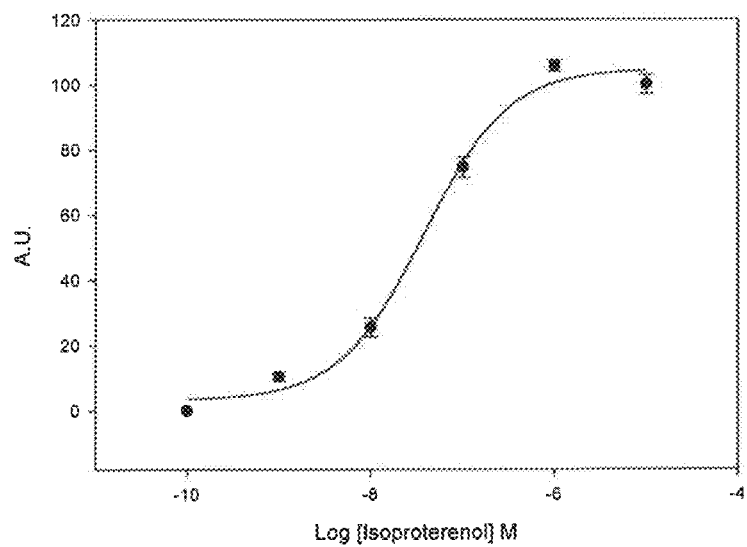
FIG. 6. Concentration response curve for Isoproterenol in Adrenergic beta 2-CAMP biosensor cell line. Cells were treated with 6 log dilution series (n=4). The Ec50 for the Isoproterenol was $2.3\times10^{-7}$ M after a treatment of 36 h with agonist. Cells were fixed and the nuclei were stained with DAPI. % Activity was calculated relative to positive (10 uM). The internalization assay was validated with an average of $Z'=0.7+/-0.01$ for High Content Screening.

To determine whether cAMP induces a significant conformational change within a physiological dynamic range, the U2O2 biosensor stable cell line was stably transfected with the human adrenergic beta 2 receptor. The adrenergic receptors are a class of G protein-coupled receptors that are targets of the catecholamines, especially noradrenaline (norepinephrine) and adrenaline (epinephrine). The double stable cell line was seeded at 20.000 cell per well on 96-mm optical plates, and cultured in 200 ul of DMEM F12 supplemented with 10% fetal bovine serum. For fluorescent biosensor redistribution, the cells were stimulated with different concentrations of Isoproterenol agonist during 36 hours (FIG. 5). After treatment, the nucleus was stained with DAPI and biosensor fluorescence redistribution was detected by fluorescence using image analysis algorithms. When cells were treated with the agonist, the biosensor was internalized from plasmatic membrane in high intensity vesicles. The activity was calculated as an increment of granularity these cells. Cells were treated with 11 log dilution series (n=5). The Ec50 for the Isoproterenol was ~2.3×10-7M after a treatment of 24 h with agonist. The redistribution assay was validated with an average of Z'=0.7+/−0.01 for High Content Screening. The results are shown in FIG. 6.

Example 3. Construction and Use of a Diacylglycerol Biosensor for Measurement of Diacylglycerol in Living Cells within a Broad Dynamic Range of Physiological Concentrations of this Second Messenger The authors of the present invention constructed a fluorescent fusion polypeptide comprising the extracellular domain of interleukin-2 receptor of SEQ ID No 17 as the membrane localization peptide, the binding sequence of SEQ ID No 19 as the second messenger transduction protein binding peptide, the peptide KDEL as the reticulum retention signal and the turboGFP as the fluorescent peptide wherein:
  a. the membrane localization peptide was located at the N-terminus of the fluorescent fusion polypeptide and was physically bound, through a linker, to the fluorescent peptide, which in turn was physically bound, through a linker, to the second messenger transduction protein binding peptide; and
  b. the second messenger transduction protein binding peptide was physically bound, through a linker, to the reticulum retention signal, which in turn was located at the C-terminus of the fluorescent fusion polypeptide.

The complete fluorescent fusion polypeptide is illustrated in SEQ ID No 18.

Figure 7:
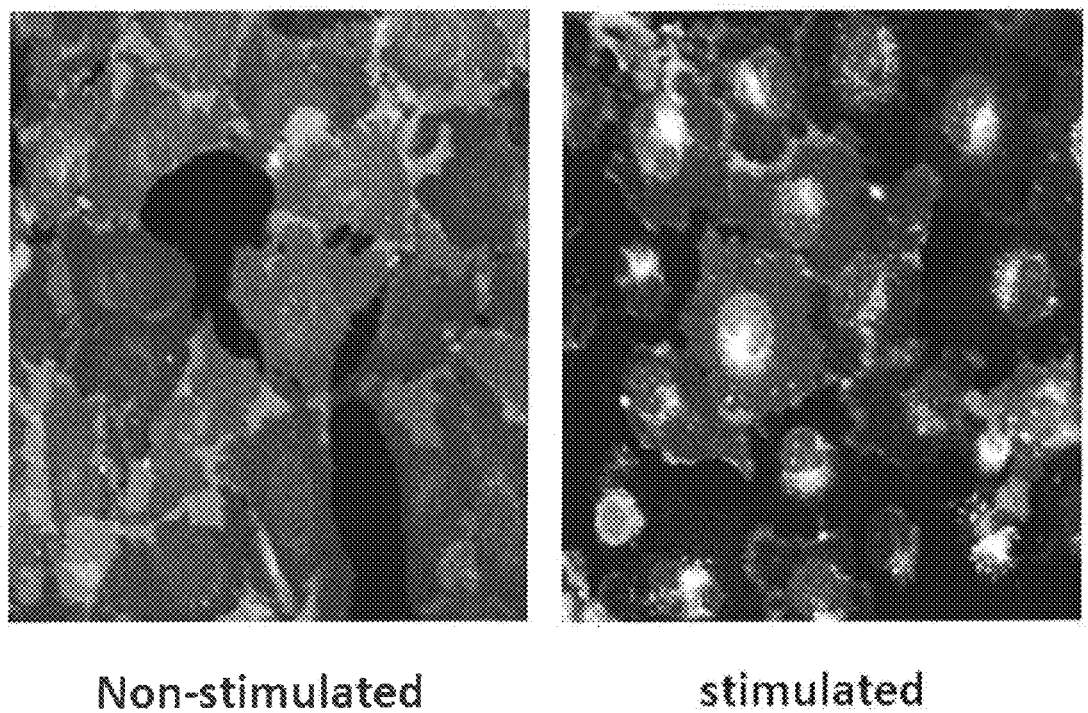
FIG. 7. Cellular distribution of DAG biosensor stimulated cells. U2OS stably expressing fluorescent DAG biosensor, were stimulated with 25 ng/ml of PMA during 4 hours. After the treatment, the fluorescent biosensor was internalized in vesicles in the citosol. DAG biosensor activity was determined measuring the generation of the vesicle using image analysis algorithms.
Figure 8:
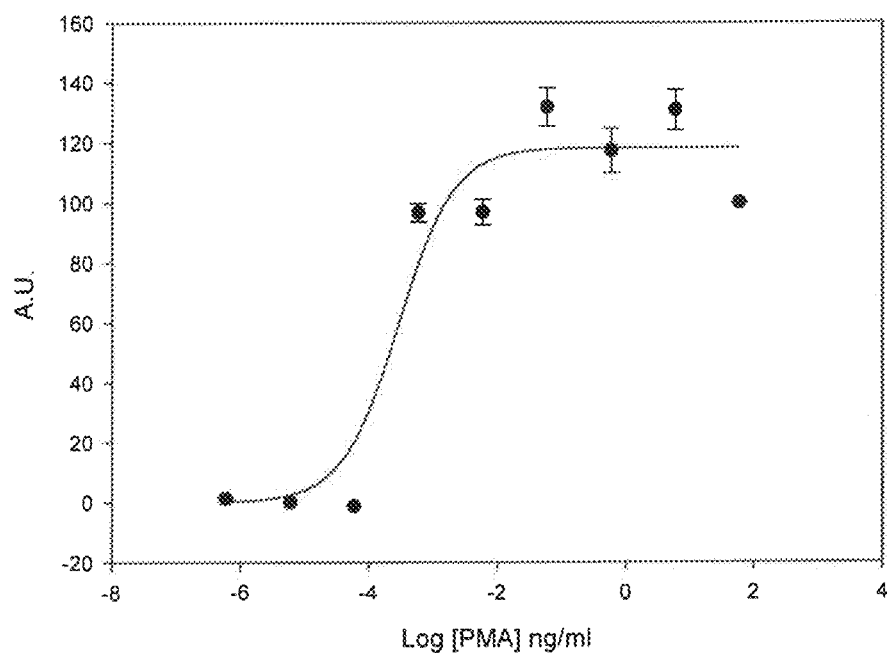
FIG. 8. Concentration response curve for DAG biosensor cell line. Cells were treated with 9 log dilution series (n=4). The Ec50 for the Isoproterenol was $2.89\times10^4$ ng/ml after a treatment of 4 h with DAG. Cells were fixed and the nuclei were stained with DAPI. % Activity was calculated relative to positive (50 ng/ml). The internalization assay was validated with an average of $Z'=0.76+/-0.01$ for High Content Screening.

As with the previous examples, in order to assess whether the activation of the above mentioned polypeptide induces intracellular fluorescence redistribution in living cells, peptide turboGFP was cloned as the fluorescent peptide and the cellular localization of the biosensor was analysed upon diacylglycerol induced activation. In this sense, U2O2 cell line was stably transfected with the plasmid construction that contains the above mentioned biosensor's coding sequence. This stably transfected cell line presented a membrane distribution of the fluorescence before inducing the activation of intracellular diacylglycerol. As with the previous examples, activity was calculated as an increment of granularity by treating these cells with increasing dosages of PMA. The results are shown in FIG. 7 and FIG. 8.

SEQUENCE LISTING

```
SEQ ID No 1:
MEKRRWKKNFIAVSAANRFKKISSSGAL

SEQ ID No 2:
ASPWKSARLMVHTVATFNSI

SEQ ID No 3:
AIGFKKLAEAVKFSAKLMGQ

SEQ ID No 4:
KKTFKEVANAVKISASLMGT

SEQ ID Na 5:
GAVLKVLTTGLPALISWIKR

SEQ ID No 6:
RGGFRRIARLVGVLREWAYR

SEQ ID No 7:
GGRLALLRARLKELAALEAA

SEQ ID No 8:
AEGVRNIKSMWEKGNVFSSP

SEQ ID No 9:
DLIEEAASRIVDAVIEQVKAAGAY

SEQ ID no 10:
VQGNTDEAQEELAWKIAKMIVSDVMQQ

SEQ ID No 11:
VQGNTDEAQEELLWKIAKMIVSDVMQQ

SEQ ID No 12:
FEELAWKIAKMIWSDVFQQ

SEQ ID No 13:
QIEYLAKQIVDNAIQQAK

SEQ ID No 14:
LEQYANLADQIIKEATE

SEQ ID No 15:
MDSYLLMWGLLTFIMVPGCQAELCDDDPPEIPHATFKAMAYKEGTMLNCECKRGFRRIKSGSLYMLCTGNSSHSSWD
NQCQCTSSATRNTTKQVTPQPEEQKERKTTEMQSPMQPVDQASLPGHCREPPPWENEATERIYHFVVGQMVYYQCVQ
GYRALHRGPAESVCKMTHGKTRWTQPQLICTGEMETSQFPGEEKPQASPEGRPESETSCLVTTTDFQIQTEMAATME
TSIFTTDLQVAVAGCVFLLISVLLLSGLTWQRRQRKSGRTIGIQLVVDQQQQQQGILQSTVPMESDESGLPAMEIEC
```

-continued

RITGTLNGVEFELVGGGEGTPEQGRMTNKMKSTKGALTFSPYLLSHVMGYGFYHFGTYPSGYENPFLHAINNGGYTN
TRIEKYEDGGVLHVSFSYRYEAGRVIGDFKVMGTGFPEDSVIFTDKIIRSNATVEHLHPMGDNDLDGSFTRTFSLRD
GGYYSSVVDSHMHFKSAIHPSILQNGGPMFAFRRVEEDHSNTELGIVEYQHAFKTPDADAGEERSREMEKRRWKKNF
IAVSAANRFKKISSSGALKDEL

SEQ ID No 16:
MDSYLLMWGLLTFIMVPGCQAELCDDDPPEIPHATFKAMAYKEGTMLNCECKRGFRRIKSGSLYMLCTGNSSHSSWD
NQCQCTSSATRNTTKQVTPQPEEQKERKTTEMQSPMQPVDQASLPGHCREPPPWENEATERIYHFVVGQMVYYQCVQ
GYRALHRGPAESVCKMTHGKTRWTQPQLICTGEMETSQFPGEEKPQASPEGRPESETSCLVTTTDFQIQTEMAATME
TSIFTTDLQVAVAGCVFLLISVLLLSGLTWQRRQRKSGRTIGIQLVVDQQQQQQGILQSTVPMESDESGLPAMEIEC
RITGTLNGVEFELVGGGEGTPEQGRMTNKMKSTKGALTFSPYLLSHVMGYGFYHFGTYPSGYENPFLHAINNGGYTN
TRIEKYEDGGVLHVSFSYRYEAGRVIGDFKVMGTGFPEDSVIFTDKIIRSNATVEHLHPMGDNDLDGSFTRTFSLRD
GGYYSSVVDSHMHFKSAIHPSILQNGGPMFAFRRVEEDHSNTELGIVEYQHAFKTPDADAGEERSRVDLIEEAASRI
VDAVIEQVKAAGAYGGKDEL

SEQ ID No 17:
MDSYLLMWGLLTFIMVPGCQAELCDDDPPEIPHATFKAMAYKEGTMLNCECKRGFRRIKSGSLYMLCTGNSSHSSWD
NQCQCTSSATRNTTKQVTPQPEEQKERKTTEMQSPMQPVDQASLPGHCREPPPWENEATERIYHFVVGQMVYYQCVQ
GYRALHRGPAESVCKMTHGKTRWTQPQLICTGEMETSQFPGEEKPQASPEGRPESETSCLVTTTDFQIQTEMAATME
TSIFTTDLQVAVAGCVFLLISVLLLSGLTWQRRQRKSGRTI

SEQ ID No 18:
MDSYLLMWGLLTFIMVPGCQAELCDDDPPEIPHATFKAMAYKEGTMLNCECKRGFRRIKSGSLYMLCTGNSSHSSWD
NQCQCTSSATRNTTKQVTPQPEEQKERKTTEMQSPMQPVDQASLPGHCREPPPWENEATERIYHFVVGQMVYYQCVQ
GYRALHRGPAESVCKMTHGKTRWTQPQLICTGEMETSQFPGEEKPQASPEGRPESETSCLVTTTDFQIQTEMAATME
TSIFTTDLQVAVAGCVFLLISVLLLSGLTWQRRQRKSGRTIGIQLVVDQQQQQQGILQSTVPMESDESGLPAMEIEC
RITGTLNGVEFELVGGGEGTPEQGRMTNKMKSTKGALTFSPYLLSHVMGYGFYHFGTYPSGYENPFLHAINNGGYTN
TRIEKYEDGGVLHVSFSYRYEAGRVIGDFKVMGTGFPEDSVIFTDKIIRSNATVEHLHPMGDNDLDGSFTRTFSLRD
GGYYSSVVDSHMHFKSAIHPSILQNGGPMFAFRRVEEDHSNTELGIVEYQHAFKTPDADAGEERSRVAARKRKGSFF
YGGKDEL

SEQ ID No 19:
AARKRKGSFFYGG

SEQ ID No 20:
MSKGEELFTGVVPILVELDGDVNGHKFSVSGEGEGDATYGKLTLKFICTTGKLPVPWPTLVTTFSYGVQCFSRYPDH
MKQHDFFKSAMPEGYVQERTIFFKDDGNYKTRAEVKFEGDTLVNRIELKGIDFKEDGNILGHKLEYNYNSHNVYIMA
DKQKNGIKVNFKIRHNIEDGSVQLADHYQQNTPIGDGPVLLPDNHYLSTQSALSKDPNEKRDHMVLLEFVTAAGITH
GMDELYK

SEQ ID No 21
MFKGIVEGIGIIEKIDIYTDLDKYAIRFPENMLNGIKKESSIMFNGCFLTVTSVNSNIVWFDIFEKEARKLDTFREY
KVGDRVNLGTFPKFGAASGGHILSARISCVASIIEIIENEDYQQMWIQIPENFTEFLIDKDYIAVDGISLTIDTIKN
NQFFISLPLKIAQNTNMKWRKKGDKVNVELSNKINANQCW

SEQ ID No 22
MESDESGLPAMEIECRITGTLNGVEFELVGGGEGTPEQGRMTNKMKSTKGALTFSPYLLSHVMGYGFYHFGTYPSGY
ENPFLHAINNGGYTNTRIEKYEDGGVLHVSFSYRYEAGRVIGDFKVMGTGFPEDSVIFTDKIIRSNATVEHLHPMGD
NDLDGSFTRTFSLRDGGYYSSVVDSHMHFKSAIHPSILQNGGPMFAFRRVEEDHSNTELGIVEYQHAFKTPDADAGE
E

SEQ ID No 23
MVSKGEELIKENMHMKLYMEGTVNNHHFKCTSEGEGKPYEGTQTMRIKVVEGGPLPFAFDILATSFMYGSRTFINHT
QGIPDFFKQSFPEGFTWERVTTYEDGGVLTATQDTSLQDGCLIYNVKIRGVNFPSNGPVMQKKTLGWEANTEMLYPA
DGGLEGRSDMALKLVGGGHLICNFKTTYRSKKPAKNLKMPGVYYVDHRLERIKEADKETYVEQHEVAVARYCDLPSK
LGHKLN

SEQ ID No 24
MVGEDSELITENMHMKLYMEGTVNNHHFKCTSEGEGKPYEGTQTMKIKVVEGGPLPFAFDILATSFMYGSKAFINHT
QGIPDFFKQSFPEGFTWERITTYEDGGVLTATQDTSLQNGCLIYNVKINGVNFPSNGPVMQKKTLGWEASTEMLYPA
DSGLRGHGQMALKLVGGGYLHCSLKTTYRSKKPAKNLKMPGFHFVDHRLERIKEADKETYVEQHEMAVAKYCDLPSK
LGHS

SEQ ID No 25
MSGGEELFAGIVPVLIELDGDVHGHKFSVRGEGEGDADYGKLEIKFICTTGKLPVPWPTLVTTLCYGIQCFARYPEH
MKMNDFFKSAMPEGYIQERTIQFQDDGKYKTRGEVKFEGDTLVNRIELKGKDFKEDGNILGHKLEYSFNSHNVYIRP
DKANNGLEANFKTRHNIEGGGVQLADHYQTNVPLGDGPVLIPINHYLSTQTKISKDRNEARDHMVLLESFSACCTHG
MDELYR

The invention claimed is:

1. A fluorescent fusion polypeptide, wherein said fluorescent fusion polypeptide is capable of changing its localization within a cell from cytoplasmic membrane to a retention vesicle upon an increase in the concentration of a second messenger in the cytoplasm of the cell, and comprises, from N- to C-terminus, a membrane localization peptide, a fluorescent peptide, a second messenger transduction protein binding peptide, and a reticulum retention signal peptide;
   wherein the second messenger is calcium; wherein the membrane localization peptide is a human IL-2R comprising the amino acid sequence of SEQ ID NO:17; and wherein the second messenger transduction protein binding peptide is a calmodulin binding peptide comprising the amino acid sequence of SEQ ID NO:1.

2. The fluorescent fusion polypeptide of claim 1, wherein the reticulum retention signal peptide is selected from the group consisting of KDEL, HDEL, KKXX, KXKXX and RXR, wherein X is any amino acid.

3. The fluorescent fusion polypeptide of claim 1, wherein the reticulum retention signal peptide is KDEL.

4. The fluorescent fusion polypeptide of claim 1, wherein the fluorescent peptide is selected from the group consisting of GFP, YFP, turboGFP, tRFP and tRFP602.

5. The fluorescent fusion polypeptide of claim 1, wherein the fluorescent peptide is selected from the group consisting of GFP, YFP, turboGFP, tRFP and tRFP602; and the reticulum retention signal peptide is KDEL.

6. The fluorescent fusion polypeptide of claim 1, wherein said polypeptide comprises the amino acid sequence of SEQ ID NO: 15.

7. A nucleic acid molecule comprising a polynucleotide sequence coding for the fluorescent fusion polypeptide of claim 1.

8. An isolated cell comprising the fluorescent fusion polypeptide of claim 1.

* * * * *

SEQUENCE LISTING

<160> NUMBER OF SEQ ID NOS: 25

<210> SEQ ID NO 1
<211> LENGTH: 28
<212> TYPE: PRT
<213> ORGANISM: Artificial Sequence

```
<220> FEATURE:
<223> OTHER INFORMATION: Calmodulin binding sequence
<220> FEATURE:
<221> NAME/KEY: PEPTIDE
<222> LOCATION: (1)..(28)

<400> SEQUENCE: 1

Met Glu Lys Arg Arg Trp Lys Lys Asn Phe Ile Ala Val Ser Ala Ala
1               5                   10                  15

Asn Arg Phe Lys Lys Ile Ser Ser Ser Gly Ala Leu
            20                  25

<210> SEQ ID NO 2
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 2

Ala Ser Pro Trp Lys Ser Ala Arg Leu Met Val His Thr Val Ala Thr
1               5                   10                  15

Phe Asn Ser Ile
            20

<210> SEQ ID NO 3
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 3

Ala Ile Gly Phe Lys Lys Leu Ala Glu Ala Val Lys Phe Ser Ala Lys
1               5                   10                  15

Leu Met Gly Gln
            20

<210> SEQ ID NO 4
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 4

Lys Lys Thr Phe Lys Glu Val Ala Asn Ala Val Lys Ile Ser Ala Ser
1               5                   10                  15

Leu Met Gly Thr
            20

<210> SEQ ID NO 5
<211> LENGTH: 20
<212> TYPE: PRT
<213> ORGANISM: Artificial Sequence
<220> FEATURE:
<223> OTHER INFORMATION: Calmodulin binding sequence
```

```
<220> FEATURE:
<221> NAME/KEY: PEPTIDE
<222> LOCATION: (1)..(20)
<223> OTHER INFORMATION: Calmodulin binding sequence

<400> SEQUENCE: 5

Gly Ala Val Leu Lys Val Leu Thr Thr Gly Leu Pro Ala Leu Ile Ser
1               5                   10                  15

Trp Ile Lys Arg
            20

<210> SEQ ID NO 6
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 6

Arg Gly Gly Phe Arg Arg Ile Ala Arg Leu Val Gly Val Leu Arg Glu
1               5                   10                  15

Trp Ala Tyr Arg
            20

<210> SEQ ID NO 7
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 7

Gly Gly Arg Leu Ala Leu Leu Arg Ala Arg Leu Lys Glu Leu Ala Ala
1               5                   10                  15

Leu Glu Ala Ala
            20

<210> SEQ ID NO 8
<211> LENGTH: 20
<212> TYPE: PRT
<213> ORGANISM: Artificial Sequence
<220> FEATURE:
<223> OTHER INFORMATION: Calmodulin binding sequence
<220> FEATURE:
<221> NAME/KEY: PEPTIDE
<222> LOCATION: (1)..(20)

<400> SEQUENCE: 8

Ala Glu Gly Val Arg Asn Ile Lys Ser Met Trp Glu Lys Gly Asn Val
1               5                   10                  15

Phe Ser Ser Pro
            20

<210> SEQ ID NO 9
<211> LENGTH: 24
<212> TYPE: PRT
<213> ORGANISM: Artificial Sequence
<220> FEATURE:
<223> OTHER INFORMATION: Binding sequence to the  RI and RII regulatory
      domains of PKA
```

```
<220> FEATURE:
<221> NAME/KEY: PEPTIDE
<222> LOCATION: (1)..(24)

<400> SEQUENCE: 9

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 10
<211> LENGTH: 27
<212> TYPE: PRT
<213> ORGANISM: Artificial Sequence
<220> FEATURE:
<223> OTHER INFORMATION: Binding sequence to the  RI and RII regulatory
      domains of PKA
<220> FEATURE:
<221> NAME/KEY: PEPTIDE
<222> LOCATION: (1)..(27)

<400> SEQUENCE: 10

Val Gln Gly Asn Thr Asp Glu Ala Gln Glu Glu Leu Ala Trp Lys Ile
1               5                   10                  15

Ala Lys Met Ile Val Ser Asp Val Met Gln Gln
            20                  25

<210> SEQ ID NO 11
<211> LENGTH: 27
<212> TYPE: PRT
<213> ORGANISM: Artificial Sequence
<220> FEATURE:
<223> OTHER INFORMATION: Binding sequence to the  RI and RII regulatory
      domains of PKA
<220> FEATURE:
<221> NAME/KEY: PEPTIDE
<222> LOCATION: (1)..(27)

<400> SEQUENCE: 11

Val Gln Gly Asn Thr Asp Glu Ala Gln Glu Glu Leu Leu Trp Lys Ile
1               5                   10                  15

Ala Lys Met Ile Val Ser Asp Val Met Gln Gln
            20                  25

<210> SEQ ID NO 12
<211> LENGTH: 19
<212> TYPE: PRT
<213> ORGANISM: Artificial Sequence
<220> FEATURE:
<223> OTHER INFORMATION: Binding sequence to the  RI and RII regulatory
      domains of PKA
<220> FEATURE:
<221> NAME/KEY: PEPTIDE
<222> LOCATION: (1)..(19)

<400> SEQUENCE: 12

Phe Glu Glu Leu Ala Trp Lys Ile Ala Lys Met Ile Trp Ser Asp Val
1               5                   10                  15

Phe Gln Gln

<210> SEQ ID NO 13
<211> LENGTH: 18
<212> TYPE: PRT
<213> ORGANISM: Artificial Sequence
<220> FEATURE:
<223> OTHER INFORMATION: Binding sequence to the  RI and RII regulatory
      domains of PKA
```

```
<220> FEATURE:
<221> NAME/KEY: PEPTIDE
<222> LOCATION: (1)..(18)

<400> SEQUENCE: 13

Gln Ile Glu Tyr Leu Ala Lys Gln Ile Val Asp Asn Ala Ile Gln Gln
1               5                   10                  15

Ala Lys

<210> SEQ ID NO 14
<211> LENGTH: 18
<212> TYPE: PRT
<213> ORGANISM: Artificial Sequence
<220> FEATURE:
<223> OTHER INFORMATION: Binding sequence to the RI and RII regulatory
      domains of PKA
<220> FEATURE:
<221> NAME/KEY: PEPTIDE
<222> LOCATION: (1)..(18)

<400> SEQUENCE: 14

Leu Glu Gln Tyr Ala Asn Gln Leu Ala Asp Gln Ile Ile Lys Glu Ala
1               5                   10                  15

Thr Glu

<210> SEQ ID NO 15
<211> LENGTH: 561
<212> TYPE: PRT
<213> ORGANISM: Artificial Sequence
<220> FEATURE:
<223> OTHER INFORMATION: Calcium fluorescent fusion polypeptide
<220> FEATURE:
<221> NAME/KEY: PEPTIDE
<222> LOCATION: (1)..(561)

<400> SEQUENCE: 15

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190
```

```
Phe Pro Gly Glu Glu Lys Pro Gln Ala Ser Pro Glu Gly Arg Pro Glu
            195                 200                 205
Ser Glu Thr Ser Cys Leu Val Thr Thr Thr Asp Phe Gln Ile Gln Thr
    210                 215                 220
Glu Met Ala Ala Thr Met Glu Thr Ser Ile Phe Thr Thr Asp Leu Gln
225                 230                 235                 240
Val Ala Val Ala Gly Cys Val Phe Leu Leu Ile Ser Val Leu Leu Leu
                245                 250                 255
Ser Gly Leu Thr Trp Gln Arg Arg Gln Arg Lys Ser Gly Arg Thr Ile
            260                 265                 270
Gly Ile Gln Leu Val Val Asp Gln Gln Gln Gln Gln Gly Ile Leu
        275                 280                 285
Gln Ser Thr Val Pro Met Glu Ser Asp Glu Ser Gly Leu Pro Ala Met
    290                 295                 300
Glu Ile Glu Cys Arg Ile Thr Gly Thr Leu Asn Gly Val Glu Phe Glu
305                 310                 315                 320
Leu Val Gly Gly Gly Glu Gly Thr Pro Glu Gln Gly Arg Met Thr Asn
                325                 330                 335
Lys Met Lys Ser Thr Lys Gly Ala Leu Thr Phe Ser Pro Tyr Leu Leu
            340                 345                 350
Ser His Val Met Gly Tyr Gly Phe Tyr His Phe Gly Thr Tyr Pro Ser
        355                 360                 365
Gly Tyr Glu Asn Pro Phe Leu His Ala Ile Asn Asn Gly Gly Tyr Thr
    370                 375                 380
Asn Thr Arg Ile Glu Lys Tyr Glu Asp Gly Gly Val Leu His Val Ser
385                 390                 395                 400
Phe Ser Tyr Arg Tyr Glu Ala Gly Arg Val Ile Gly Asp Phe Lys Val
                405                 410                 415
Met Gly Thr Gly Phe Pro Glu Asp Ser Val Ile Phe Thr Asp Lys Ile
            420                 425                 430
Ile Arg Ser Asn Ala Thr Val Glu His Leu His Pro Met Gly Asp Asn
        435                 440                 445
Asp Leu Asp Gly Ser Phe Thr Arg Thr Phe Ser Leu Arg Asp Gly Gly
    450                 455                 460
Tyr Tyr Ser Ser Val Val Asp Ser His Met His Phe Lys Ser Ala Ile
465                 470                 475                 480
His Pro Ser Ile Leu Gln Asn Gly Gly Pro Met Phe Ala Phe Arg Arg
                485                 490                 495
Val Glu Glu Asp His Ser Asn Thr Glu Leu Gly Ile Val Glu Tyr Gln
            500                 505                 510
His Ala Phe Lys Thr Pro Asp Ala Asp Ala Gly Glu Glu Arg Ser Arg
        515                 520                 525
Glu Met Glu Lys Arg Arg Trp Lys Lys Asn Phe Ile Ala Val Ser Ala
    530                 535                 540
Ala Asn Arg Phe Lys Lys Ile Ser Ser Ser Gly Ala Leu Lys Asp Glu
545                 550                 555                 560
Leu

<210> SEQ ID NO 16
<211> LENGTH: 559
<212> TYPE: PRT
<213> ORGANISM: Artificial Sequence
<220> FEATURE:
<223> OTHER INFORMATION: cAMP fluorescent fusion polypeptide
```

```
<220> FEATURE:
<221> NAME/KEY: PEPTIDE
<222> LOCATION: (1)..(559)

<400> SEQUENCE: 16

Met Asp Ser Tyr Leu Leu Met Trp Gly Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
50                      55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
210                 215                 220

Glu Met Ala Ala Thr Met Glu Thr Ser Ile Phe Thr Thr Asp Leu Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Gly Arg Thr Ile
            260                 265                 270

Gly Ile Gln Leu Val Val Asp Gln Gln Gln Gln Gln Gly Ile Leu
            275                 280                 285

Gln Ser Thr Val Pro Met Glu Ser Asp Glu Ser Gly Leu Pro Ala Met
290                 295                 300

Glu Ile Glu Cys Arg Ile Thr Gly Thr Leu Asn Gly Val Glu Phe Glu
305                 310                 315                 320

Leu Val Gly Gly Gly Glu Gly Thr Pro Glu Gln Gly Arg Met Thr Asn
                325                 330                 335

Lys Met Lys Ser Thr Lys Gly Ala Leu Thr Phe Ser Pro Tyr Leu Leu
            340                 345                 350

Ser His Val Met Gly Tyr Gly Phe Tyr His Phe Gly Thr Tyr Pro Ser
            355                 360                 365

Gly Tyr Glu Asn Pro Phe Leu His Ala Ile Asn Asn Gly Gly Tyr Thr
370                 375                 380
```

```
Asn Thr Arg Ile Glu Lys Tyr Glu Asp Gly Val Leu His Val Ser
385                 390                 395                 400

Phe Ser Tyr Arg Tyr Glu Ala Gly Arg Val Ile Gly Asp Phe Lys Val
                405                 410                 415

Met Gly Thr Gly Phe Pro Glu Asp Ser Val Ile Phe Thr Asp Lys Ile
            420                 425                 430

Ile Arg Ser Asn Ala Thr Val Glu His Leu His Pro Met Gly Asp Asn
        435                 440                 445

Asp Leu Asp Gly Ser Phe Thr Arg Thr Phe Ser Leu Arg Asp Gly Gly
    450                 455                 460

Tyr Tyr Ser Ser Val Val Asp Ser His Met His Phe Lys Ser Ala Ile
465                 470                 475                 480

His Pro Ser Ile Leu Gln Asn Gly Gly Pro Met Phe Ala Phe Arg Arg
                485                 490                 495

Val Glu Glu Asp His Ser Asn Thr Glu Leu Gly Ile Val Glu Tyr Gln
            500                 505                 510

His Ala Phe Lys Thr Pro Asp Ala Asp Ala Gly Glu Glu Arg Ser Arg
        515                 520                 525

Val Asp Leu Ile Glu Glu Ala Ala Ser Arg Ile Val Asp Ala Val Ile
    530                 535                 540

Glu Gln Val Lys Ala Ala Gly Ala Tyr Gly Gly Lys Asp Glu Leu
545                 550                 555

<210> SEQ ID NO 17
<211> LENGTH: 272
<212> TYPE: PRT
<213> ORGANISM: Artificial Sequence
<220> FEATURE:
<223> OTHER INFORMATION: Extracellular domain of Interleukin-2 Receptor
<220> FEATURE:
<221> NAME/KEY: PEPTIDE
<222> LOCATION: (1)..(272)

<400> SEQUENCE: 17

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175
```

-continued

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
            210                 215                 220

Glu Met Ala Ala Thr Met Glu Thr Ser Ile Phe Thr Thr Asp Leu Gln
225                 230                 235                 240

Val Ala Val Ala Gly Cys Val Phe Leu Leu Ile Ser Val Leu Leu Leu
            245                 250                 255

Ser Gly Leu Thr Trp Gln Arg Arg Gln Arg Lys Ser Gly Arg Thr Ile
            260                 265                 270

<210> SEQ ID NO 18
<211> LENGTH: 546
<212> TYPE: PRT
<213> ORGANISM: Artificial Sequence
<220> FEATURE:
<223> OTHER INFORMATION: DAG fluorescent fusion polypeptide
<220> FEATURE:
<221> NAME/KEY: PEPTIDE
<222> LOCATION: (1)..(546)

<400> SEQUENCE: 18

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
            85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
            130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
            165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
            210                 215                 220

Glu Met Ala Ala Thr Met Glu Thr Ser Ile Phe Thr Thr Asp Leu Gln
225                 230                 235                 240

Val Ala Val Ala Gly Cys Val Phe Leu Leu Ile Ser Val Leu Leu Leu
            245                 250                 255

-continued

```
Ser Gly Leu Thr Trp Gln Arg Arg Gln Arg Lys Ser Gly Arg Thr Ile
            260                 265                 270

Gly Ile Gln Leu Val Val Asp Gln Gln Gln Gln Gln Gly Ile Leu
        275                 280                 285

Gln Ser Thr Val Pro Met Glu Ser Asp Glu Ser Gly Leu Pro Ala Met
    290                 295                 300

Glu Ile Glu Cys Arg Ile Thr Gly Thr Leu Asn Gly Val Glu Phe Glu
305                 310                 315                 320

Leu Val Gly Gly Gly Glu Gly Thr Pro Glu Gln Gly Arg Met Thr Asn
                325                 330                 335

Lys Met Lys Ser Thr Lys Gly Ala Leu Thr Phe Ser Pro Tyr Leu Leu
            340                 345                 350

Ser His Val Met Gly Tyr Gly Phe Tyr His Phe Gly Thr Tyr Pro Ser
        355                 360                 365

Gly Tyr Glu Asn Pro Phe Leu His Ala Ile Asn Asn Gly Gly Tyr Thr
    370                 375                 380

Asn Thr Arg Ile Glu Lys Tyr Glu Asp Gly Gly Val Leu His Val Ser
385                 390                 395                 400

Phe Ser Tyr Arg Tyr Glu Ala Gly Arg Val Ile Gly Asp Phe Lys Val
                405                 410                 415

Met Gly Thr Gly Phe Pro Glu Asp Ser Val Ile Phe Thr Asp Lys Ile
            420                 425                 430

Ile Arg Ser Asn Ala Thr Val Glu His Leu His Pro Met Gly Asp Asn
        435                 440                 445

Asp Leu Asp Gly Ser Phe Thr Arg Thr Phe Ser Leu Arg Asp Gly Gly
    450                 455                 460

Tyr Tyr Ser Ser Val Val Asp Ser His Met His Phe Lys Ser Ala Ile
465                 470                 475                 480

His Pro Ser Ile Leu Gln Asn Gly Gly Pro Met Phe Ala Phe Arg Arg
                485                 490                 495

Val Glu Glu Asp His Ser Asn Thr Glu Leu Gly Ile Val Glu Tyr Gln
            500                 505                 510

His Ala Phe Lys Thr Pro Asp Ala Asp Ala Gly Glu Glu Arg Ser Arg
        515                 520                 525

Val Ala Ala Arg Lys Arg Lys Gly Ser Phe Phe Tyr Gly Gly Lys Asp
    530                 535                 540

Glu Leu
545

<210> SEQ ID NO 19
<211> LENGTH: 13
<212> TYPE: PRT
<213> ORGANISM: Artificial Sequence
<220> FEATURE:
<223> OTHER INFORMATION: Binding sequence to PKCdelta
<220> FEATURE:
<221> NAME/KEY: PEPTIDE
<222> LOCATION: (1)..(13)

<400> SEQUENCE: 19

Ala Ala Arg Lys Arg Lys Gly Ser Phe Phe Tyr Gly Gly
1               5                   10

<210> SEQ ID NO 20
<211> LENGTH: 238
<212> TYPE: PRT
<213> ORGANISM: Artificial Sequence
```

```
<220> FEATURE:
<223> OTHER INFORMATION: Green Fluorescent Protein (GFP)
<220> FEATURE:
<221> NAME/KEY: PEPTIDE
<222> LOCATION: (1)..(238)

<400> SEQUENCE: 20

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 21
<211> LENGTH: 194
<212> TYPE: PRT
<213> ORGANISM: Artificial Sequence
<220> FEATURE:
<223> OTHER INFORMATION: YFP
<220> FEATURE:
<221> NAME/KEY: PEPTIDE
<222> LOCATION: (1)..(194)

<400> SEQUENCE: 21

Met Phe Lys Gly Ile Val Glu Gly Ile Gly Ile Ile Glu Lys Ile Asp
1               5                   10                  15

Ile Tyr Thr Asp Leu Asp Lys Tyr Ala Ile Arg Phe Pro Glu Asn Met
            20                  25                  30

Leu Asn Gly Ile Lys Lys Glu Ser Ser Ile Met Phe Asn Gly Cys Phe
        35                  40                  45

Leu Thr Val Thr Ser Val Asn Ser Asn Ile Val Trp Phe Asp Ile Phe
    50                  55                  60
```

```
Glu Lys Glu Ala Arg Lys Leu Asp Thr Phe Arg Glu Tyr Lys Val Gly
 65                  70                  75                  80

Asp Arg Val Asn Leu Gly Thr Phe Pro Lys Phe Gly Ala Ala Ser Gly
                 85                  90                  95

Gly His Ile Leu Ser Ala Arg Ile Ser Cys Val Ala Ser Ile Ile Glu
            100                 105                 110

Ile Ile Glu Asn Glu Asp Tyr Gln Gln Met Trp Ile Gln Ile Pro Glu
        115                 120                 125

Asn Phe Thr Glu Phe Leu Ile Asp Lys Asp Tyr Ile Ala Val Asp Gly
    130                 135                 140

Ile Ser Leu Thr Ile Asp Thr Ile Lys Asn Asn Gln Phe Phe Ile Ser
145                 150                 155                 160

Leu Pro Leu Lys Ile Ala Gln Asn Thr Asn Met Lys Trp Arg Lys Lys
                165                 170                 175

Gly Asp Lys Val Asn Val Glu Leu Ser Asn Lys Ile Asn Ala Asn Gln
            180                 185                 190

Cys Trp

<210> SEQ ID NO 22
<211> LENGTH: 232
<212> TYPE: PRT
<213> ORGANISM: Artificial Sequence
<220> FEATURE:
<223> OTHER INFORMATION: TurboGFP
<220> FEATURE:
<221> NAME/KEY: PEPTIDE
<222> LOCATION: (1)..(232)
<220> FEATURE:
<221> NAME/KEY: PEPTIDE
<222> LOCATION: (1)..(232)

<400> SEQUENCE: 22

Met Glu Ser Asp Glu Ser Gly Leu Pro Ala Met Glu Ile Glu Cys Arg
  1               5                  10                  15

Ile Thr Gly Thr Leu Asn Gly Val Glu Phe Glu Leu Val Gly Gly Gly
             20                  25                  30

Glu Gly Thr Pro Glu Gln Gly Arg Met Thr Asn Lys Met Lys Ser Thr
         35                  40                  45

Lys Gly Ala Leu Thr Phe Ser Pro Tyr Leu Leu Ser His Val Met Gly
 50                  55                  60

Tyr Gly Phe Tyr His Phe Gly Thr Tyr Pro Ser Gly Tyr Glu Asn Pro
 65                  70                  75                  80

Phe Leu His Ala Ile Asn Asn Gly Gly Tyr Thr Asn Thr Arg Ile Glu
                 85                  90                  95

Lys Tyr Glu Asp Gly Gly Val Leu His Val Ser Phe Ser Tyr Arg Tyr
            100                 105                 110

Glu Ala Gly Arg Val Ile Gly Asp Phe Lys Val Met Gly Thr Gly Phe
        115                 120                 125

Pro Glu Asp Ser Val Ile Phe Thr Asp Lys Ile Ile Arg Ser Asn Ala
    130                 135                 140

Thr Val Glu His Leu His Pro Met Gly Asp Asn Asp Leu Asp Gly Ser
145                 150                 155                 160

Phe Thr Arg Thr Phe Ser Leu Arg Asp Gly Gly Tyr Tyr Ser Ser Val
                165                 170                 175

Val Asp Ser His Met His Phe Lys Ser Ala Ile His Pro Ser Ile Leu
            180                 185                 190
```

```
Gln Asn Gly Gly Pro Met Phe Ala Phe Arg Arg Val Glu Glu Asp His
            195                 200                 205

Ser Asn Thr Glu Leu Gly Ile Val Glu Tyr Gln His Ala Phe Lys Thr
210                 215                 220

Pro Asp Ala Asp Ala Gly Glu Glu
225                 230
```

<210> SEQ ID NO 23
<211> LENGTH: 237
<212> TYPE: PRT
<213> ORGANISM: Artificial Sequence
<220> FEATURE:
<223> OTHER INFORMATION: TagRFP
<220> FEATURE:
<221> NAME/KEY: PEPTIDE
<222> LOCATION: (1)..(237)

<400> SEQUENCE: 23

```
Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
50                  55                  60

Ser Phe Met Tyr Gly Ser Arg Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Pro Ser Asn Gly Pro Val Met Gln Lys Lys Thr Leu Gly Trp
130                 135                 140

Glu Ala Asn Thr Glu Met Leu Tyr Pro Ala Asp Gly Gly Leu Glu Gly
145                 150                 155                 160

Arg Ser Asp Met Ala Leu Lys Leu Val Gly Gly Gly His Leu Ile Cys
                165                 170                 175

Asn Phe Lys Thr Thr Tyr Arg Ser Lys Lys Pro Ala Lys Asn Leu Lys
            180                 185                 190

Met Pro Gly Val Tyr Tyr Val Asp His Arg Leu Glu Arg Ile Lys Glu
        195                 200                 205

Ala Asp Lys Glu Thr Tyr Val Glu Gln His Glu Val Ala Val Ala Arg
210                 215                 220

Tyr Cys Asp Leu Pro Ser Lys Leu Gly His Lys Leu Asn
225                 230                 235
```

<210> SEQ ID NO 24
<211> LENGTH: 235
<212> TYPE: PRT
<213> ORGANISM: Artificial Sequence
<220> FEATURE:
<223> OTHER INFORMATION: TurboFP602
<220> FEATURE:
<221> NAME/KEY: PEPTIDE
<222> LOCATION: (1)..(235)

<400> SEQUENCE: 24

Met Val Gly Glu Asp Ser Glu Leu Ile Thr Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Lys Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Lys Ala Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Ile Thr Thr Tyr Glu Asp Gly Gly Val Leu Thr Ala Thr Gln Asp Thr
            100                 105                 110

Ser Leu Gln Asn Gly Cys Leu Ile Tyr Asn Val Lys Ile Asn Gly Val
        115                 120                 125

Asn Phe Pro Ser Asn Gly Pro Val Met Gln Lys Lys Thr Leu Gly Trp
130                 135                 140

Glu Ala Ser Thr Glu Met Leu Tyr Pro Ala Asp Ser Gly Leu Arg Gly
145                 150                 155                 160

His Gly Gln Met Ala Leu Lys Leu Val Gly Gly Gly Tyr Leu His Cys
                165                 170                 175

Ser Leu Lys Thr Thr Tyr Arg Ser Lys Lys Pro Ala Lys Asn Leu Lys
            180                 185                 190

Met Pro Gly Phe His Phe Val Asp His Arg Leu Glu Arg Ile Lys Glu
        195                 200                 205

Ala Asp Lys Glu Thr Tyr Val Glu Gln His Glu Met Ala Val Ala Lys
    210                 215                 220

Tyr Cys Asp Leu Pro Ser Lys Leu Gly His Ser
225                 230                 235

<210> SEQ ID NO 25
<211> LENGTH: 238
<212> TYPE: PRT
<213> ORGANISM: Artificial Sequence
<220> FEATURE:
<223> OTHER INFORMATION: TagGFP2
<220> FEATURE:
<221> NAME/KEY: PEPTIDE
<222> LOCATION: (1)..(238)

<400> SEQUENCE: 25

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

-continued

```
Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg
225                 230                 235
```